United States Patent [19]

Inoue

[11] Patent Number: 5,380,508
[45] Date of Patent: Jan. 10, 1995

[54] CALCIUM BORATE OVERBASED SILICYLATE AS AN ADDITIVE FOR PETROLEUM PRODUCTS

[75] Inventor: Kiyoshi Inoue, Hiratsuka, Japan
[73] Assignee: Nippon Oil Co., Ltd., Tokyo, Japan
[21] Appl. No.: 112,091
[22] Filed: Aug. 26, 1993

Related U.S. Application Data

[63] Continuation-in-part of Ser. No. 878,772, May 5, 1992, Pat. No. 5,262,140, which is a continuation of Ser. No. 563,032, Aug. 6, 1990, abandoned.

[30] Foreign Application Priority Data

Aug. 9, 1989 [JP] Japan ................................. 1-204887

[51] Int. Cl.$^6$ ............................................ C01B 35/12
[52] U.S. Cl. .................................... 423/286; 252/33.6; 252/39; 252/49.6
[58] Field of Search ............... 423/286, 290; 252/33.6, 252/39, 49.6

[56] References Cited

U.S. PATENT DOCUMENTS

| | | | |
|---|---|---|---|
| 4,668,409 | 5/1987 | Yamaguchi et al. | 252/32.7 E |
| 4,683,126 | 7/1987 | Inoue et al. | 423/280 |
| 4,734,211 | 3/1988 | Kennedy | 252/51.5 A |
| 4,744,929 | 5/1988 | Robinson et al. | 261/97 |
| 4,965,004 | 10/1990 | Schlicht et al. | 252/38 |
| 5,013,463 | 5/1991 | Slama | 252/18 |
| 5,064,545 | 11/1991 | Steckel | 252/32.7 |
| 5,102,560 | 4/1992 | Davis | 252/8.554 |
| 5,160,652 | 11/1992 | Small, Jr. et al. | 252/49.6 |
| 5,262,140 | 11/1993 | Inoue | 423/286 |

FOREIGN PATENT DOCUMENTS

1239421  7/1988  Canada .

*Primary Examiner*—Gary P. Straub
*Assistant Examiner*—Timothy C. Vanoy
*Attorney, Agent, or Firm*—Bucknam and Archer

[57] ABSTRACT

This invention provides a calcium borate overbased salicylate as an additive for petroleum products which has been overbased with meta-calcium borate having a particle diameter of not larger than 200 angstrom, said meta-calcium borate being prepared by two steps of (1) reacting a mixture of (A) 100 parts by weight of oil-soluble calcium salicylate, (B) 10 to 200 parts by weight, of calcium hydroxide or oxide, (C) 1.5 to 2.5 moles, per mole of said component B, of orthoboric acid, (D) 60 to 200 parts by weight of an alkanol of 1 to 4 carbon atoms, (E) 1 to 40 parts by weight of water and (F) 40 to 1000 parts by weight of a diluent which is a nonpolar organic solvent having a boiling point of 60° C. or higher, at a temperature of from 20° to 120° C. for 2 to 8 hours, and then (2) heating the reaction mixture to 100° to 200° C. thereby to remove the water therefrom by distillation.

4 Claims, No Drawings

CALCIUM BORATE OVERBASED SILICYLATE AS AN ADDITIVE FOR PETROLEUM PRODUCTS

This application is a continuation-in-part of U.S. Ser. No. 07/878,772 filed May 5, 1992, now U.S. Pat. No. 5,262,140, which was a continuation of 07/563,032 filed Aug. 6, 1990, now abandoned.

BACKGROUND OF THE INVENTION

1. Field of the Invention

This invention relates to a calcium borate overbased salicylate for use as an additive for petroleum products and more particularly to a calcium borate overbased salicylate having extremely fine meta-calcium borate particles with a particle diameter of not more than 200 angstrom are uniformly dispersed therein and exhibiting excellent performances as a multifunctional additive for petroleum products.

2. Prior Art

A boron compound serves to improve the oxidation stability, rust-preventing properties, friction reducing properties and extreme pressure properties of a lubricating oil. Further, it has recently been found that an alkaline earth borate has excellent acid neutralizing properties and excellent hydrolytic stability when compared with conventional calcium carbonate. Under such circumstances, many research workers have attempted to incorporate stably a boron compound in the form of an alkaline earth metal borate in a lubricating oil. Especially, processes for stabilizing an alkaline earth metal borate in the form of ultramicroparticles in an oil by using a metallic detergent, for example, an alkaline earth metal sulfonate or an alkaline earth metal salicylate as a protective colloid have been studied.

For example, U.S. Pat. No. 3,679,584 discloses a process comprising reacting an overbased alkaline earth metal carbonate, namely, an overbased alkaline earth metal sulfonate with boric acid and an alkaline earth metal hydroxide in a mineral oil or a diluent by heating lo while blowing carbon dioxide into the reaction system. Further, U.S. Pat. Nos. 3,829,381, 4,744,920, etc., disclose processes comprising reacting an overbased alkaline earth metal sulfonate with boric acid in a mineral oil. Furthermore. U.S. Pat. No. 4,539,126 discloses a process for reacting an alkaline earth metal carbonate overbased compound, namely, an overbased alkaline earth metal salicylate with boric acid in a diluent by heating.

According to these processes, the alkaline earth metal dispersions are prepared by the steps of reacting an alkaline earth metal carbonate dispersed in an overbased alkaline earth metal sulfonate or salicylate with boric acid which is a weak acid and then converting the surface of the thus obtained reaction product to an alkaline earth metal borate. Therefore, it is impossible in the conventional processes to obtain alkaline earth metal borate particles having such a uniform structure and small diameter as those obtained by directly reacting calcium hydroxide or oxide which is a strong base with orthoboric acid to prepare a calcium borate dispersion as in the present invention. In addition, the reaction ratio in the conventional processes will decrease because a part of the produced alkaline earth metal borate settles due to agglomeration of the dispersed particles during the reaction. Further, the alkaline earth metal dispersions prepared by these conventional methods are poor in various performances as an additive for petroleum products as compared with calcium borate overbased salicylate dispersions obtained by the present invention. On the other hand, the inventor of this invention disclosed in U.S. Pat. No. 4,539,126 (Japanese Patent Application Laid-Open No. 204298/1986) that an alkaline earth metal borate overbased sulfonate could be produced by reacting water with boric acid and an alkaline earth metal hydroxide or oxide by heating in an oil solution a neutral alkaline earth metal sulfonate, namely, by a one-stage reaction.

However, it turned out that the process disclosed in the Japanese Patent Laid-Open No. 204298/1986 could not provide any product of a high total base number, namely, a high-boron content product when it was applied to the production of an alkaline earth metal borate overbased salicylate, though it was suitable for the production of an alkaline earth metal borate overbased sulfonate.

SUMMARY OF THE INVENTION

It is an object of this invention to provides a calcium borate overbased salicylate excellent in detergent dispersion properties, extreme pressure properties, friction and abrasion resistance, corrosion preventing properties, rust preventing properties, hydrolytic stability and acid neutralizing properties as an additive for petroleum products.

The inventor of this invention has made intensive studies of a process for producing a calcium borate overbased salicylate to accomplish the abovementioned object and has found that a calcium borate overbased salicylate obtained by a specific production process is one which is overbased with meta-calcium borate having a very small particle diameter of not larger than 200 angstrom and very excellent performances as an additive for petroleum products, thus accomplishing this invention.

Namely, this invention provides a calcium borate overbased salicylate as an additive for petroleum products which is overbased with meta-calcium borate having a particle diameter of not larger than 200 angstrom, said calcium borate overbased salicylate being prepared by the two steps of:

(1) reacting a mixture of
 (A) 100 parts by weight of oil-soluble neutral calcium salicylate,
 (B) 10 to 200 parts by weight of calcium hydroxide or oxide,
 (C) 1.5 to 2.5 moles of orthoboric acid per mole of said ingredient B,
 (D) 60 to 200 parts by weight of an alkanol of 1 to 4 carbon atoms,
 (E) 1 to 40 parts by weight of water and
 (F) 40 to 1000 parts by weight of a diluent which is a nonpolar organic solvent having a boiling point of at least 60° C. at a temperature of from 20° to 120° C. for 2 to 8 hours, and then
(2) heating the reaction mixture to 100° to 200° C. thereby to remove the water therefrom by distillation.

DETAILED DESCRIPTION OF THE INVENTION

This invention will now be described in more detail.

Component A mentioned in step (1) (hereinafter referred to as the reaction step) of this invention is an oil-soluble neutral calcium salicylate (normal salt) of a molecular weight of about 200 to 500 can be used. Examples of these compounds include those prepared by the production processes disclosed in Japanese Patent Application Laid-Open No. 101196/1985, Japanese Patent Publication No. 35325/1973 and U.S. Pat. No. 4,668,409.

Component B mentioned In the reaction step of this invention is calcium hydroxide or calcium oxide.

The amount of component B used in the reaction step is 10 to 200 parts by weight, desirably 20 to 100 parts by weight per 100 parts by weight of component A.

Component C mentioned in the reaction step of tills invention is orthoboric acid. The amount of component C used in the reaction step is 1.5 to 2.5 moles, desirably 1.8 to 2.2 moles per mole of component B.

Component D mentioned in the reaction step of this invention is an alkanol having 1 to 4 carbon atoms. A desirable component D is a monoalkanol or a dialkanol, and examples thereof include methanol, ethanol, propanol, butanol, ethylene glycol, propylene glycol, triethylene glycol, butylene glycol, tetramethylene glycol and mixtures thereof. The amount of component D used in the reaction step is 20 to 1000 parts by weight, desirably 60 to 600 parts by weight per 100 parts by weight of component A.

Component E mentioned in the reaction step of this invention is wailer. By mixing the water with the abovementioned component D at an appropriate ratio in the reaction step, the formed alkaline earth metal borate particles become very fine, and the amount of coarse particles to be removed in the final filtration step can be decreased. The amount of component E used in the reaction step is 1 to 40 parts by weight, desirably 2 to 20 parts by weight per 100 parts by weight of component A.

Component F mentioned in the reaction step of this invention is a diluent which is a nonpolar organic solvent having a boiling point of 60° C. or higher. Examples of the diluent include aromatic hydrocarbons such as benzene, toluene and xylene, petroleum-derived solvents such as benzinc, ligroin, mineral spirit and cleaning solvents and a gasoline fraction, a kerosene fraction, a gas oil fraction and a lubricating oil fraction of a mineral oil. It is to be noted that component F includes the mineral oil used as a dispersion medium for component A, i.e., a neutral calcium salicylate.

The amount of component F used in the reaction step of this invention is 40 to 1000 parts by weight, desirably 200 to 600 parts by weight per 100 parts by weight of component A.

Although the diluent as component F is used from the beginning as a dispersion medium for component A in the form of a mixture thereof with component A, it is also possible to add, if necessary, a diluent which is the same as or different from this dispersion medium in the reaction step.

In the reaction step of this invention, specified amounts of the abovementioned components A to F are reacted with each other under thorough agitation at a reaction temperature of 20° to 100° C., desirably 40° to 95° C. In this invention, the reaction is desirably carried out at atmospheric pressure in the abovementioned reaction temperature range. Although the reaction time is 2 to 8 hours, desirably 3 to 5 hours.

The reaction mixture obtained in this way is subjected to the subsequent step (2) (hereinafter referred to as the distillation step). While agitating the reaction mixture, the system is heated to 100° to 200° C., desirably 110° to 160° C. and kept at that temperature for usually 1 to 2 hours to remove the water from the system. In this distillation step, the water added as component E in the reaction step and the water formed by the reaction can be removed while the extent of hydration of the formed calcium borate can be suitably regulated. It is also possible to remove part of the alkanol as component D or the diluent as component E or the both in this step, if required.

The calcium borate dispersion obtained through the abovementioned reaction and distillation steps may be further purified, if necessary, by means of filtration or the like in order to remove remaining unreacted material and coarse particles of calcium borate.

The calcium borate dispersion obtained by the process of this invention usually contains 5 to 30 wt. % of calcium borate. This content can be freely varied by varying the mixing ratio of calcium hydroxide or oxide as component B and orthoboric acid as component C to neutral calcium salicylate as component A in the reaction step.

The meta-calcium borate which is an overbasic component in the calcium borate overbased salicylate of the present invention has the following composition:

$CaO \cdot B_2O_3 \cdot xH_2O$ wherein x represents a positive integer of from 0 to 10 and the value of x can be varied by varying the temperature and time used in the dewatering step. Further, the particle diameter of this meta-calcium borate is not larger than 200 angstrom, preferably not larger than 100 angstrom, and more preferably not larger than 50 angstrom.

The main feature of the calcium borate overbased salicylate according to the present invention is that the overbasic component is meta-calcium borate having a uniform structure and has a very small particle diameter of not larger than 200 angstrom.

The calcium borate overbased salicylate of the present invention has a high boron to calcium molar ratio of 1.0 to 2.5, preferably 1.5 to 2.2 according to an overall compositional analysis. The boron content originates from the component (C) used in the present invention, and the calcium originates from the components (A) and (B) used in the present invention. The calcium borate overbased salicylate of the present invention has a high total base number (according to the perchloric acid method) of 100 to 300, preferably 150 to 250 mgKOH/g. It is another prominent feature of the calcium borate overbased salicylate of the present invention that the overbased salicylate has such a high boron to calcium molar ratio and high total base number.

The calcium borate overbased salicylate of the present invention has excellent detergent dispersing properties, friction and abrasion resistance, extreme pressure properties, rust preventing properties, corrosion preventing properties, acid neutralizing properties and hydrolytic stability, so that it can be used as it is or as it is diluted with a proper solvent as an additive for petroleum products such as fuel oils, lubricating oils, special-purpose petroleum products and grease. The "petroleum products" defined herein include not only products derived from mineral oils as a base oil but also those derived from synthetic oils as a base oil.

Mineral oil-type base oils include refined paraffinic, naphthenic and aromatic oils prepared by subjecting solvent fractions and lubricating oil fractions obtained by the atmospheric distillation or reduced-pressure distillation of crude oils, to a suitable combination of refining treatments such as solvent deasphalting, solvent extraction, hydrocracking, solvent dewaxing, caltalytic dewaxing, hydrorefining, sulfuric acid washing and clay treating.

Synthetic oil-type base oils include poly-α-olefins (such as polypropylene, polybutene, 1-octene oligomer and 1-decene oligomer) and hydrides thereof; alkylbenzenes; alkyLnaphthalenes; diesters such as ditridecyl glutaratex, di-2-ethylhexyl adipate, diisodecyl adipate, ditridecyl adipate and di-2-ethylhexyl sebacate; polyol esters such as trimethylolpropane caprylate, trimethylolpropane pelargonate, pentaerythritol 2-ethylhexanoate and pentaerythritol pelargonate; polyoxyalkylene glycol; polyphenyl ether; and synthesized naphtenes.

These mineral oil- and synthetic oil-type base oils may be used alone or jointly.

Feul oils in which the calcium borate overbased salicylate of the present invention may be used, include a crude oil, gasoline, naphtha, feuls for jet engines, kerosine, light oil and heavy oil. The lubricating oils in which the overbased salicylate of the present invention may be used, include engine oils such as a four-cycle gasoline engine oil, a two-cycle gasoline engine oil, a diesel engine oil for land and a diesel engine oil for ships; turbine oils such as an added turbine oil, a gas turbine oil and a turbine oil for ships; gear oils such as a gear oil for cars, an automatic transmission oil and an industrial gear oil; hydraulic oils; compressor oils; vacuum pump oils; refrigerator oils; metal working oils such as a cutting oil, a grinding oil, a plastic working oil (a milling oil, a drawing oil, a solid drawing oil, a punch working oil and a press oil), a thermal treating oil, and an electrical discharge machining oil; a sliding guide oil (a machine tool oil); and a bearing oil. The special-purpose petroleum products include an electrical insulating oil, a rust preventing oil and a thermal medium oil.

The amount off calcium borate overbased salicylate of the present invention added to petroleum products may be arbitrary, but it is 0.0001 to 1% by weight, preferably 0.0005 to 0.5% by weight, based on the total weight of the resulting composition when added to a fuel oil. On the other hand, in a case where the calcium borate overbased salicylate of the present invention is used in lubricating oils, special purpose petroleum products and grease, it is added in an amount of 0.1 to 50% by weight, preferably 0.5 to 30% by weight, based on the total weight of the resulting composition.

The calcium borate overbased salicylates of the present invention typically include calcium borate overbased alkylsalicylates.

The compound "alkylsalicylate" defined herein is one having one or two alkyl groups with carbon atoms of 12 to 30, preferably 14 to 20. Although the position of substitution of the alkyl group in the alkylsalicylate is arbitrary, it is usually at the 3-position and/or 5-position of salicylic acid.

Examples of the alkyl group in the alkylsalicylates of this invention are dodecyl (including branched isomeric groups), tridecyl (including branched isomeric groups), tetradecyl (including branched isomeric groups), pentadecyl (including branched isomeric groups), hexadecyl (including branched isomeric groups), heptadecyl (including branched isomeric groups), octadecyl (including branched isomeric groups), nonadecyl (including branched isomeric groups), eicosyl (including branched isomeric groups), heneicosyl (including branched isomeric groups), docosyl (including branched isomeric groups), tocosyl (including branched isomeric groups), tetracosyl (including branched isomeric groups), pentacosyl (including branched isomeric groups), hexacosyl (including branched isomeric groups), heptacosyl (including branched isomeric groups), octacosyl (including branched isomeric groups), nonacosyl (including branched isomeric groups) and triacontyl (including branched isomeric groups) groups.

Further, preferable alkylsalicylates in this invention are ones substituted with one or two alkyl groups at the 3-position and/or 5-position thereof, the alkyl groups being derived from an α-olefine having carbon atoms of 12 to 30, preferably 14 to 20.

Effects of the Invention

As so far described, it is possible to obtain the calcium borate overbased salicylate of the present invention by a very simple one-stage reaction process. In addition to this, the calcium borate overbased salicylate so obtained has a high reaction ratio and a high total base number close to the theoretical value since it is prepared by directly reacting calcium hydroxide or oxide, which is a strong base, with orthoboric acid in the presence of oil-soluble neutral calcium salicylate. Further, the basic component of calcium borate overbased salicylate is uniform and fine meta-calcium borate particles having not larger than 200 angstrom prepared by the above reaction and therefore, the calcium borate overbased salicylate of the present invention has extremely excellent performances as a multi-functional additive for petroleum products.

EXAMPLE

This invention will be better understood by the following Example and Comparative Examples.

The alkylsalicylate used in the Example and Comparative Examples is a mixture of alkylsalicylates substituted with an alkyl group at their 3-position and/or 5-position, the alkyl group being one which is derived from an equimolar mixture of 1-hexadecene and 1-octadecene.

EXAMPLE 1

Two hundred (200) grams of a neutral calcium alkylsalicylate (calcium content; 2.0 wt. %) (A), which had been diluted to an extent of effective concentration of 50% by weight with a lubricating oil fraction, 26 g of calcium hydroxide (B), 43.4 g (2.0 moles per mole of calcium hydroxide) of orthoboric acid (C) and 400 g of xylene (F) were put in a 1000-ml four-necked flask fitted with a condenser and heated to 60° C. while agitating. To this mixture were added 120 g of methanol (D) and 20 g of water (E), and the resulting mixture was heated up to a refluxing temperature (66° C.) under agitation and reacted for 4 hours. The reaction mixture was further heated to 140° C. for 1.5 hours to distill out the methanol, water and xylene. Finally the reaction product was diluted twofold with hexane and filtered to remove any residual solids present, and the hexane was distilled out to obtain a desired calcium borate overbased alkylsalicylate.

The results obtained by the transmission-type electron microscopic observation of the thus obtained calcium borate overbased alkylsalicylate showed that the calcium borate which was an overbasic component had a particle diameter of not more than 50 angstrom. Further, 5% by weight of water and 1% by weight of methanol were added to the calcium borate overbased alkylsalicylate to obtain a mixture which was agitated at 93.5 C for 24 hours with the use of an apparatus prescribed in ASTM D2619 to precipitate the calcium borate which was an overbasic component and dispersed in the mixture and then centrifuged to collect precipitated calcium borate. The thus collected calcium borate was measured with an X-ray analyser with the result that it was found to be meta-calcium borate.

COMPARATIVE EXAMPLE 1

200 g of the same neutral calcium alkylsalicylate (A) as used in Example 1, 26 g of calcium hydroxide (B), 43.4 g (2.0 moles per mole of the calcium hydroxide) of orthoboric acid (C) and 400 g of xylene (F) were put in a 1000-ml four-necked flask fitted with a condenser and heated to 60° C. while agitating. To this mixture was added 20 g of water, and the resulting mixture was heated up to a refluxing temperature (66° C.) under agitation and reacted for 4 hours to obtain a reaction product. The reaction product was further heated to 140° C. for 1.5 hours to distill out the water and xylene. Finally the reaction product was diluted twofold with hexane and filtered to remove any residual solids present, and the hexane was distilled out to obtain a calcium borate overbased alkylsalicylate.

COMPARATIVE EXAMPLE 2

200 g of the same neutral calcium alkylsalicylate (A) as used in Example 1, 26 g of calcium hydroxide (B), 43.4 g (2.0 moles per mole of the calcium hydroxide) of orthoboric acid (C) and 400 g of xylene (F) were put in a 1000-ml four-necked flask fitted with a condenser and heated to 60° C. while agitating. To this mixture was added 120 g of methanol, and the resulting mixture was heated up to a refluxing temperature (66° C.) under agitation and reacted for 4 hours to obtain a reaction product. The reaction product was further heated to 140° C. for 1.5 hours to distill out the methanol, reaction water and xylene. Finally the reaction product was diluted twofold with hexane and filtered to remove any residual solids present, and the hexane was distilled out to obtain a calcium borate overbased alkylsalicylate. However, the thus obtained calcium borate overbased alkylsalicylate caused its gelation and was found generally unusable as an additive for petroleum products.

COMPARATIVE EXAMPLE 3

A solution or 323.2 g of a calcium carbonate overbased alkylsalicylate (TBN 205 mgKOH/g, calcium content; 8.5 wt. %) (the calcium content of this starting material being the same as the total calcium content of the starting materials (A) and (B) in Example 1 or in each of Comparative Examples 1 and 2) and 400 g of xylene were put in a 1000-ml four-necked flask fitted with a condenser and heated to 60° C. while agitating. To this mixture was added 43.4 g of orthoboric acid, and the resulting mixture was heated up to a refluxing temperature (66° C.) under agitation and reacted for 4 hours to obtain a reaction product. The reaction product was further heated to 140° C. for 1.5 hours to distill out the reaction water and xylene. Finally the reaction product was diluted twofold with hexane and filtered to remove any residual solids present, and the hexane was distilled out to obtain a calcium borate overbased alkylsalicylate.

COMPARATIVE EXAMPLE 4

A solution of 200 g of a calcium carbonate overbased alkylsalicylate (TBN 280 mgKOH/g, calcium content; 10.0 wt. %) and 200 g of xylene were put in a 1000-ml four-necked flask fitted with a condenser and heated to 95° C. while agitating. To this mixture was added 20 g of orthoboric acid, and the temperature was gradually increased to 145° C., while the reaction water was removed by azeotropic distillation by spending time for 1.5 hours. Subsequently, the reactor contents were filtered to obtain a filtrate (solution) which was cooled and then centrifuged to remove any residual solids present. Finally, the xylene was removed in vacuo to obtain a calcium borate overbased alkylsalicylate.

Test and Evaluation (1) Properties of various calcium borate overbased alkylsalicylates Properties of various calcium borate overbased alkylsalicylates thus obtained were measured.

The results obtained are shown in Table A.

TABLE A

|  | Example 1 | Comp. Ex. 1 | Comp. Ex. 3 | Comp. Ex. 4 |
|---|---|---|---|---|
| Base Number[1] (ASTM D664) | 200 [205] | 90 [205] | 135 [205] | 245 [280] |
| Element Ca | 7.0 | 3.1 | 3.5 | 9.2 |
| Analysis wt % B | 3.1 | 0.7 | 1.3 | 1.4 |
| B/Ca (molar ratio) | 1.6 | 0.2 | 0.7 | 0.3 |
| B/Ca (molar ratio)[2] | 2.1 | 2.3 | 1.6 | 0.7 |

[1]The values shown in parentheses are ones calculated on the assumption that the reaction ratio is 100%.
[2]5% by weight of water and 1% by weight of methanol were added to each of the calcium borate overbased alkylsalicylates to obtain a mixture which was agitated at 93.5 C. for 24 hours with the use of an apparatus prescribed in ASTM D2619 to settle the calcium borate, the overbasic component, dispersed in the mixture and centrifuge the mixture thereby to collect the settled calcium borate. The calcium borate so collected was subjected to elemental analysis for calcium and boron whereby B/Ca (molar ratio) was found by calculation.

As is apparent from Table A showing the measured properties of the calcium borate overbased alkylsalicylates obtained in Example 1 and Comparative Examples 1, 3 and 4. the desired calcium borate overbased alkylsalicylate of the present invention (Example 1) can be prepared substantially without precipitating the calcium borate due to its agglomeration at the time of manufacture of said desired overbased alkylsalicylate, and the base number thereof is approximate to the theoretical one thereof calculated on the assumption that the reaction rate is 100%, this showing a very high actual reaction rate.

On the other hand, it is found that both the calcium borate overbased alkylsalicylate of Comparative Example 1 which is prepared without the addition of methanol (D), and those of Comparative Examples 3 and 4 which are prepared by reacting only a calcium borate overbased alkylsalicylate and orthoboric acid with each other, are manufactured at a lower reaction rate than in Example 1 due to agglomeration of a large quantity of the calcium borate during the manufacture of the final overbased products with the result that these comparative calcium borate overbased alkylsalicylates have a very low base number.

Furthermore, the boron to calcium (B/Ca) molar ratios of the calcium borate dispersed in the calcium borate overbased alkylsalicylates of Comparative Examples 3 and 4 are low as compared with that of Example 1 according to the present invention. This shows that the calcium borate dispersed in the calcium borate overbased alkylsalicylates of Comparative Examples 3 and 4 is not uniform in structure unlike the meta-calcium borate prepared by directly reacting calcium hydroxide which is a strong base, with orthoboric acid as in the present invention since the calcium borate dispersed in the calcium borate overbased alkylsalicylates of Comparative Examples 3 and 4 is prepared by reacting the calcium carbonate dispersed in the calcium carbonate overbased alkylsalicylate with orthoboric acid which is a weak acid to convert the surface of said original alkylsalicylate into calcium borate.

(2) Performances of various calcium borate overbased alkylsalicylates (A) Oxidation Stability Test Test oils were prepared by dissolving each salicylate and a package of API SG Grade in which a metallic detergent is removed, in a solvent refined mineral oil (10.2 cSt at 100° C.). The test oils thus prepared were evaluated according to the thin film oxygen absorption test prescribed in ASTM D4742. The results obtained are shown in Table B.

This Table B shows that the longer the induction time is, the more excellent the oxidation stability is. Furthermore, each salicylate was added to adjust the base number to 4.5 mgKOH/g according to ASTM D4742 of the test oil.

TABLE B

|  | Example 1 | Comp. Ex. 1 | Comp. Ex. 3 | Comp. Ex. 4 |
| --- | --- | --- | --- | --- |
| Oxidation stability induction time (min) | 153 | 128 | 135 | 132 |

(B) Wear Resistance Test

Test oils were prepared by dissolving each salicylate in a solvent refined mineral oil (10.2 cSt at 100° C.). Using each of the test oils, the sear diameter (mm) produced by wear was measured in terms of wear resistance in accordance with "Wear preventive characteristics of lubricating fluid (HIGH SPEED FOURBALL METHOD)" prescribed in ASTM D4172 under the condition of 1,200 rpm, 30 kgf, 30 min and an oil temperature of 80° C.

The result obtained are shown in Table C.

This Table C shows that the smaller the value of the sear diameter is the more excellent the wear resistance is. Furthermore, each salicylate was added to adjust the base number to 4.5 mgKOH/g according to ASTM D4742 of the test oil.

TABLE C

|  | Example 1 | Comp. Ex. 1 | Comp. Ex. 3 | Comp. Ex. 4 |
| --- | --- | --- | --- | --- |
| Sear diameter (mm) | 0.42 | 0.55 | 0.53 | 0.47 |

As is apparent from the test results of performaces in Tables B and C, the calcium borate overbased alkylsalicylates of Comparative Examples 1, 3 and 4 not only have a base number much lower than the theoretical one thereof because of their low reaction rate, but also are poor in oxidation stability and wear resistance as compared with the overbased alkylsalicylates of the present invention even if said comparative overbased alkylsalicylates are added to a base oil in such an amount that the resulting test oil has the same base number as that in which the overbased alkylsalicylate of the present invention is incorporated. Thus, it is apparent that the calcium borate overbased alkylsalicylates of the present invention are superlot as an additive for petroleum products.

What is claimed is:

1. A calcium borate overbased salicylate as an additive for petroleum products which has been overbased with meta-calcium borate having a particle diameter of not larger than 200 angstrom, said meta-calcium borate being prepared by two steps of:
   (1) reacting a mixture of
      (A) 100 parts by weight of oil-soluble neutral calcium salicylate,
      (B) 10 to 200 parts by weight of calcium hydroxide or oxide,
      (C) 1.5 to 2.5 moles, per mole of said component (B), of orthoboric acid,
      (D) 60 to 200 parts by weight of an alkanol of 1 to 4 carbon atoms,
      (E) 1 to 40 parts by weight of water and
      (F) 40 to 1000 parts by weight of a diluent which is a nonpolar organic solvent having a boiling point of at least 60° C., and heating the reaction mixture at a temperature of from 20° to 120° C. for 2 to 8 hours, and then
   (2) heating the reaction mixture to 100° to 200 ° C. thereby to remove the water therefrom by distillation.

2. The calcium borate overbased salicylate according to claim 1 wherein said mixture in step (1) contains said neutral calcium salicylate of molecular weight between 200 and 500.

3. The calcium borate overbased salicylate according to claim 1 which is overbased with meta calcium borate of formula $CaO.B_2O_3.xH_2O$.

4. The calcium borate overbased salicylate according to claim 1 which has high boron to calcium molar ratio of 1.0 to 2.5 and high total base number of 100–300.

* * * * *